United States Patent
Park et al.

(10) Patent No.: US 9,091,720 B2
(45) Date of Patent: Jul. 28, 2015

(54) DETECTION SYSTEM USING MAGNETIC RESISTANCE SENSOR

(75) Inventors: Jong Won Park, Seoul (KR); Chung Wan Lee, Seoul (KR); Jeong Ryul Kim, Seoul (KR)

(73) Assignee: LG LIFE SCIENCES LTD., Seoul (KR)

( * ) Notice: Subject to any disclaimer, the term of this patent is extended or adjusted under 35 U.S.C. 154(b) by 335 days.

(21) Appl. No.: 13/817,317

(22) PCT Filed: Aug. 19, 2011

(86) PCT No.: PCT/KR2011/006160
§ 371 (c)(1),
(2), (4) Date: Feb. 15, 2013

(87) PCT Pub. No.: WO2012/023840
PCT Pub. Date: Feb. 23, 2012

(65) Prior Publication Data
US 2013/0147473 A1 Jun. 13, 2013

(30) Foreign Application Priority Data
Aug. 19, 2010 (KR) .................. 10-2010-0080513

(51) Int. Cl.
*G01R 33/09* (2006.01)
*G01N 27/74* (2006.01)

(52) U.S. Cl.
CPC .............. *G01R 33/096* (2013.01); *G01N 27/74* (2013.01)

(58) Field of Classification Search
CPC ....................................................... G01R 33/09
USPC ....................................................... 324/252
See application file for complete search history.

(56) References Cited

U.S. PATENT DOCUMENTS

| 6,716,642 B1* | 4/2004 | Wu et al. ........................ 436/518 |
| 8,945,469 B2* | 2/2015 | Tsukamoto et al. ............. 422/50 |
| 2003/0049869 A1* | 3/2003 | Prinz et al. ..................... 436/526 |
| 2005/0087000 A1* | 4/2005 | Coehoorn et al. ........... 73/53.01 |
| 2008/0024118 A1* | 1/2008 | Kahlman et al. .............. 324/204 |
| 2008/0218157 A1* | 9/2008 | Tondra et al. ................. 324/204 |
| 2008/0309329 A1* | 12/2008 | Kahlman et al. .............. 324/228 |

FOREIGN PATENT DOCUMENTS

| JP | 2009-115529 | 5/2009 |
| KR | 10-2009-0044390 A | 5/2009 |
| KR | 10-2010-0054354 A | 5/2010 |

OTHER PUBLICATIONS

International Search Report for PCT/KR2011/006160 dated Mar. 28, 2012.

\* cited by examiner

*Primary Examiner* — Bot Ledynh
(74) *Attorney, Agent, or Firm* — Birch, Stewart, Kolasch & Birch, LLP

(57) ABSTRACT

Provided is a detection system using a magnetic resistance sensor. The detection system includes a magnetic resistance sensor for detecting a magnetic element of a specimen containing a magnetic particle. An external magnetic-field application device applies external magnetic fields to the magnetic resistance sensor in first and second directions, and has a space for entrance or exit of a specimen holding unit. A horizontal drive module receives the specimen holding unit to horizontally move the specimen holding unit under the magnetic resistance sensor. A vertical drive module receives the magnetic resistance sensor to vertically move the magnetic resistance sensor to the specimen holding unit.

15 Claims, 5 Drawing Sheets

DETECTION SYSTEM USING MAGNETIC RESISTANCE SENSOR

TECHNICAL FIELD

The present invention relates to a high sensitive detection system for quantitatively measuring magnetic particles using a magnetic resistance sensor.

BACKGROUND ART

A device for testing or examining the presence of one or a plurality of substance(s) in a liquid sample, for example, urine or a blood sample is referred to as a diagnosis kit or a measuring cartridge. To be specific, current diagnostic fields are being integrated into point-of-care testing (POCT). The POCT is defined as medical testing that is conducted outside a central testing room and can be performed even by ordinary people having no special skill or knowledge. At present, a diagnostic area of the POCT is spread to an individual at a site as well as a hospital.

For example, the POCT may be applied to examine the quantity of antibiotics in blood by taking a small quantity of blood after a large dose of antibiotics are administered to a patient in a hospital so as to prevent infection, or may be applied to rapidly examine a kind of medicine taken in a body so as to guarantee appropriate treatment in the case of an unexpressive child or a patient who takes a massive dose of medicine because of cognitive impairment.

An example of a medical instrument or a measuring instrument making a diagnosis using the diagnosis kit includes an electrochemical blood analyzer, an optical blood analyzer, a measuring instrument using a magnetic-field measuring method, etc. The electrochemical blood analyzer is operated so that it draws a voltage, a current, and a resistance from the measuring cartridge and uses the values for measurement. The optical blood analyzer is operated so that it acquires an image of a test line of the measuring cartridge and measures a pixel intensity of the acquired image.

FIG. 1 is a conceptual view illustrating a sensing principle of a magnetic resistance sensor. For the convenience of description, the sensing principle will be described with reference to a giant magnetoresistance (GMR) sensor as an example of the magnetic resistance sensor. This shows a spin-valve type GMR device. As shown in the drawing, the magnetic resistance sensor is configured such that a non-magnetic metal layer is fitted between two ferromagnetic metal layers. Magnetism of the first ferromagnetic metal layer is fixed, and magnetism of the second ferromagnetic layer is variably adjusted, so that only electrons having spin oriented in a specific direction pass through a conductor when the magnetism of the second layer is parallel to that of the first layer. That is, there occurs a difference in electric potential or electric resistance induced in material depending on the magnetization directional alignment between the two ferromagnetic layers, and the difference is detected as a digital signal. The GMR device has a conductor as an interlayer material. The diagnosis instrument using the magnetic resistance sensor is a high sensitive POCT device capable of quantitatively measuring magnetic particles accumulated in a lateral flow membrane using the GMR sensor.

Such a measuring instrument using magnetic resistance requires greater automation, and needs to be implemented as standardized automatic equipment to improve a quantitative measuring quality.

DISCLOSURE OF INVENTION

Technical Problem

An aspect of the present invention is directed to a signal detection system for a specimen using a magnetic resistance sensor, configured so that magnetic fields are applied to the magnetic resistance sensor in Y-axis and Z-axis directions of the magnetic resistance sensor to maximize sensitivity of the sensor, and a horizontal movement of a specimen holding unit and a vertical movement of the magnetic resistance sensor are implemented to achieve a more accurate measuring result.

Solution to Problem

According to an embodiment of the present invention, there is provided a detection system using a magnetic resistance sensor including a magnetic resistance sensor for detecting a magnetic element of a specimen containing a magnetic particle; an external magnetic-field application device for applying external magnetic fields to the magnetic resistance sensor in first and second directions, the external magnetic-field application device having a space for entrance or exit of a specimen holding unit; a horizontal drive module for receiving the specimen holding unit to horizontally move the specimen holding unit under the magnetic resistance sensor; and a vertical drive module for receiving the magnetic resistance sensor to vertically move the magnetic resistance sensor to the specimen holding unit.

According to another embodiment of the present invention, the horizontal drive module may include an assay unit for receiving the specimen holding unit, and a feeding unit and a Y-axis drive motor for moving the assay unit under the magnetic resistance sensor.

According to another embodiment of the present invention, the vertical drive module may include a support unit for supporting the magnetic resistance sensor, and a Z-axis drive motor for vertically moving the magnetic resistance sensor to the specimen holding unit moved by the horizontal drive module.

According to another embodiment of the present invention, the detection system may further include a control unit for analyzing a detection signal of the magnetic resistance sensor to control a movement of the drive motor.

According to another embodiment of the present invention, the detection system may further include a casing for accommodating the detection system, a display unit for displaying an analysis result of the detection signal to an outside of the casing, and a printing unit for outputting the analysis result of the detection signal to an outside.

According to another embodiment of the present invention, the external magnetic-field application device may include a first application unit for applying a magnetic field to the magnetic resistance sensor in a horizontal direction (Y-axis) that is the first direction, and a second application unit for applying a magnetic field to the magnetic resistance sensor in a vertical direction (Z-axis) that is the second direction.

According to another embodiment of the present invention, the specimen holding unit having the specimen may comprise a measuring cartridge or a membrane to which a combination of a magnetic particle and an antibody is fixed.

According to another embodiment of the present invention, the first application unit may comprise a magnetic-field generating unit including one or more components selected from a group consisting of a solenoid coil, a Helmholtz coil, an electro-magnetic yoke, and a permanent magnet, thus applying a fixed magnetic field.

According to another embodiment of the present invention, the second application unit may comprise a magnetic-field generating unit including one or more components selected from a group consisting of a solenoid coil, a Helmholtz coil, and an electro-magnetic yoke, thus applying a magnetic field.

According to another embodiment of the present invention, the magnetic field generated by the second application unit may be formed by a DC current.

According to another embodiment of the present invention, the magnetic resistance sensor according to the present invention may comprise a GMR sensor.

Advantageous Effects of Invention

According to the present invention, a signal detection system for a specimen using a magnetic resistance sensor is advantageous in that magnetic fields are applied to the magnetic resistance sensor in Y-axis and Z-axis directions of the magnetic resistance sensor, thus maximizing sensitivity of the sensor, and a horizontal movement of a specimen holding unit and a vertical movement of the magnetic resistance sensor are implemented, thus achieving a more accurate measuring result.

Further, a body diagnosis can be efficiently performed by sensing a specimen using a non-contact type giant magnetoresistance sensor. Thereby, a measuring device for effectively measuring a membrane can be developed by installing the membrane used in a Point of Care Testing (POCT) in a specimen diagnosis kit. Further, the system can be driven only using DC power, so that the system may be driven by power less than power for a conventional hall sensor, and thereby is advantageous economically.

BRIEF DESCRIPTION OF DRAWINGS

The above and other aspects, features and advantages of certain exemplary embodiments of the present invention will be more apparent from the following description taken in conjunction with the accompanying drawings, in which:

FIGS. 5(a) to 5(e) are views showing the internal configuration of the detection system of FIG. 4, in which FIGS. 5(a), 5(b), 5(c), 5(d), and 5(e) are a top plan view, a left side view, a front view, a right side view, and a rear view of the detection system, respectively;

REFERENCE NUMERALS

Figure 1:
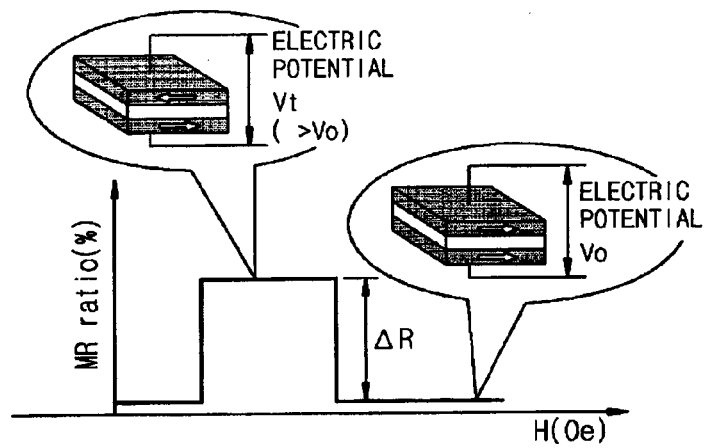
FIG. 1 is a conceptual view illustrating a sensing principle of a magnetic resistance sensor.

110: input section
120: separation pad
130: binding pad
140: measurement section (porous membrane)
150: absorption pad
210: external magnetic-field application device
201: specimen
202: specimen holding unit
230: magnetic resistance sensor
300: horizontal drive module
310: assay unit
311: guide rail
320: X-axis drive motor
400: horizontal drive module
410: support unit
420: Z-axis drive motor

MODE FOR THE INVENTION

Exemplary embodiments of the present invention will be described below in detail with reference to the accompanying drawings. Wherever possible, the same reference numerals will be used to refer to the same elements throughout the specification, and a duplicated description thereof will be omitted. It will be understood that although the terms "first", "second", etc. are used herein to describe various elements, these elements should not be limited by these terms. These terms are only used to distinguish one element from another element.

Figure 2:
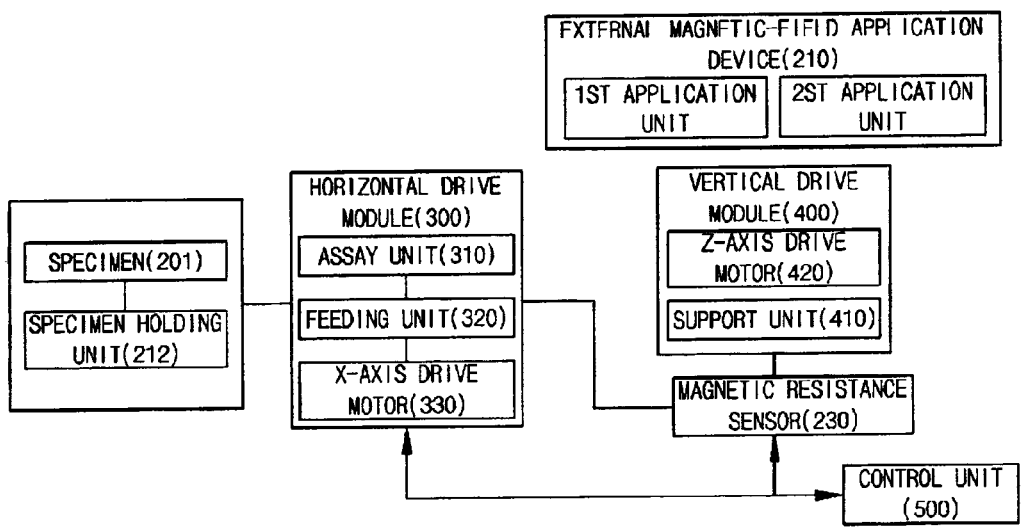
FIG. 2 is a block diagram showing a detection system using a magnetic resistance sensor in accordance with the present invention.

FIG. 2 is a block diagram showing a detection system using a magnetic resistance sensor in accordance with the present invention.

The detection system according to the present invention includes a magnetic resistance (MR) sensor 230 to detect magnetic elements of a specimen 201 containing magnetic particles, and an external magnetic-field application device 210 that applies external magnetic fields in first and second directions of the magnetic resistance sensor and has a space for entrance or exit of a specimen holding unit 202. Further, the detection system includes a horizontal drive module 300 that receives the specimen holding unit 202 to horizontally move the specimen holding unit 202 under the magnetic resistance sensor, and a vertical drive module 400 that receives the magnetic resistance sensor to vertically move the magnetic resistance sensor to the specimen holding unit 202.

In detail, in order to detect the magnetic element of the specimen, the external magnetic-field application device 210 applies magnetic fields from an outside. The external magnetic-field application device 210 may include a first application unit 211 that applies a magnetic field to the magnetic resistance sensor 230 in a horizontal direction that is the first direction, and a second application unit 212 that applies a magnetic field to the magnetic resistance sensor 230 in a vertical direction that is the second direction.

Through such a basic configuration, the specimen is mounted on the specimen holding unit 202, the external magnetic-field application device 210 applies external magnetic fields, and the magnetic resistance sensor 230 detects a magnetic signal for the specimen coupled with the magnetic element (magnetic particle) to separate and analyze the signal as an electric element. The magnetic particles may have a magnetization value of 10 to 100 emu/g. In this case, the magnetic particle has characteristics of superparamagnetism or paramagnetism. Further, the specimen holding unit 202 for holding the specimen 201 may be a measuring cartridge or a membrane.

If the external magnetic-field application device 210 applying a magnetic field to the magnetic resistance sensor in at least one direction is used, an intensity of a magnetic force exerted on magnetic particles in a bio-substance is equal to the sum of intensities of magnetic fields applied in the horizontal and vertical directions, so that a magnetizing force of the bio-substance is increased and thus sensitivity is improved.

For more efficient measurement, the specimen holding unit 202 on which the specimen is mounted needs to be fed to a magnetic field area formed by the external magnetic-field application device. In this case, the horizontal drive module 300 is required to receive the specimen holding unit and moves the specimen holding unit under the magnetic resistance sensor. Further, the vertical drive module 400 performing a vertical movement is required to make the magnetic resistance sensor approach the specimen holding unit that has horizontally moved to a detection area, for high sensitive measurement. Furthermore, the detection system may include a control unit 500 to analyze the detected magnetic signal and control the movements of the vertical and horizontal drive modules.

The detection system according to the present invention configured as described above will be described in detail with reference to FIGS. 2 to 4.

Figure 3:
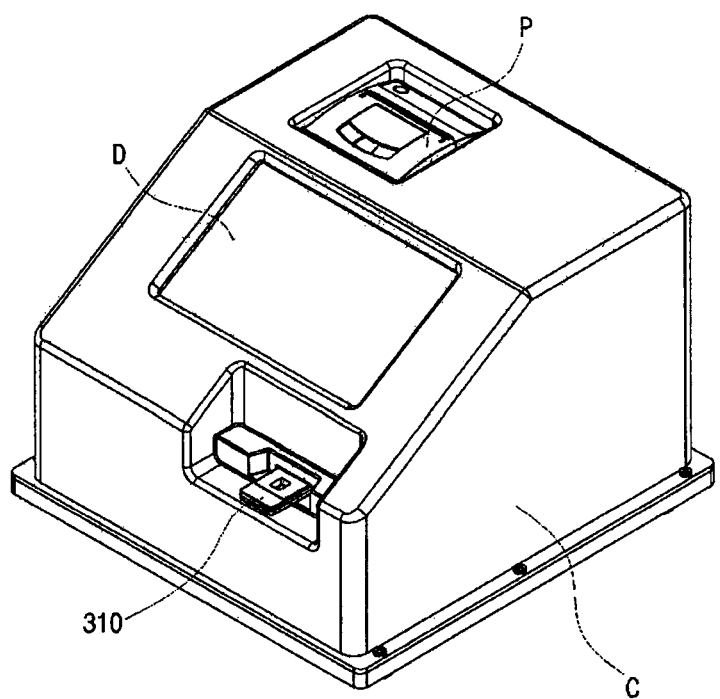
FIG. 3 is a view showing an embodiment of an external shape of the detection system in accordance with the present invention.

FIG. 3 is a view showing an embodiment of an external shape of the detection system in accordance with the present invention. An end of an assay unit 310 protrudes to the outside to permit the insertion of the specimen holding unit, e.g. a cartridge. The detection system may also include a display unit D to display a result obtained after the detection has been completed, and a printing unit to print the result.

Figure 4:
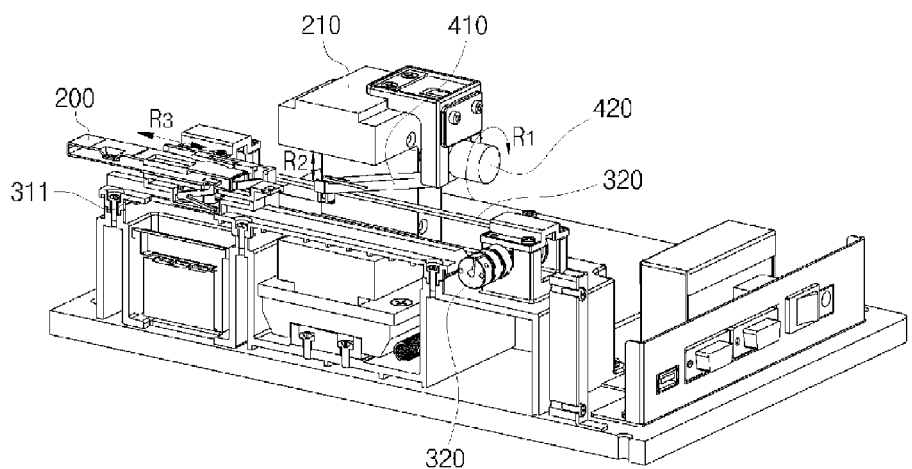
FIG. 4 is a view showing an internal configuration of the detection system of FIG. 3.
Figure 5:
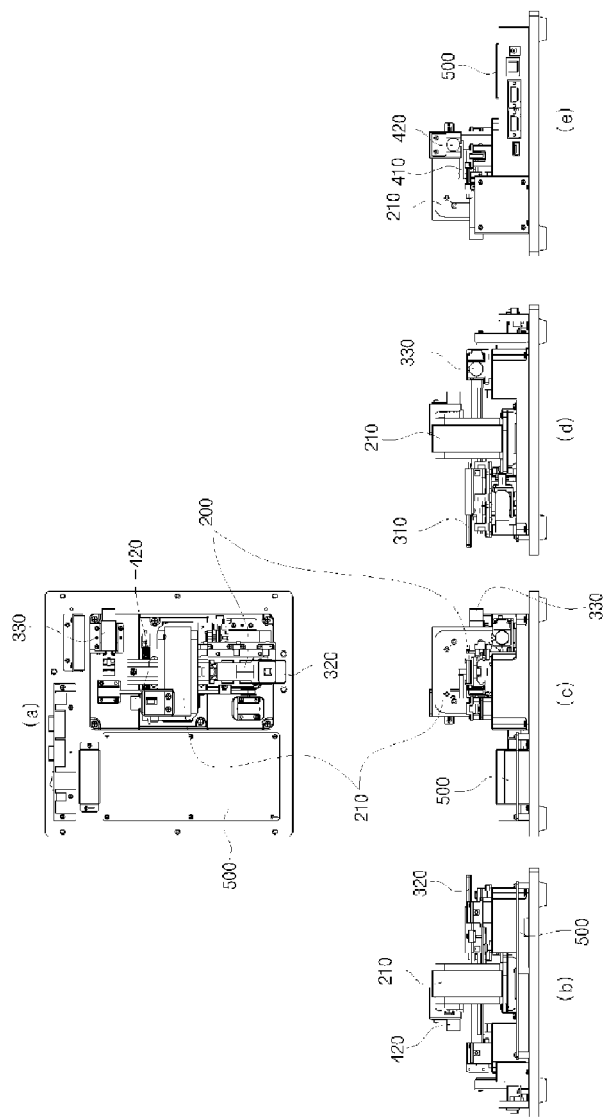

FIG. 4 is a view showing an internal configuration of the detection system of FIG. 3.

Referring to FIG. 4, if the specimen holding unit is inserted into the assay unit 310, the control unit 500 moves the assay unit 310 horizontally (reciprocates in a direction of R3) to the detection area having the magnetic field under the external magnetic-field application device 210. Such a horizontal movement is performed by the horizontal movement module 300. The horizontal movement module 300 receives a driving force of a Y-axis drive motor 330 (rotates in a direction of R1) by a feeding unit, such as a belt, for horizontally moving the assay unit 310, thus feeding the assay unit 310 under the external magnetic-field application device 210. The assay unit 310 moves along a guide rail 311.

If the assay unit 310 reaches the detection area formed under the external magnetic-field application device 210 by a driving operation of the horizontal movement module 300, the control unit drives a Z-axis drive motor 420 to operate the vertical drive module 400, thus moving the magnetic resistance sensor 230 up and down (in a direction of R2) at an end of the support unit 410 that supports the magnetic resistance sensor 230 in such a way that it moves up and down.

The magnetic resistance sensor 230 is moved down by the support unit 410 and then is stopped above the specimen holding unit 202 inserted into the assay unit 310 so as to detect a magnetic signal. For more accurate detection, it is preferable that the assay unit be controlled by the control unit to be reciprocated in the same direction as a measuring direction of the magnetic resistance sensor, thus measuring the maximum value of a variable electric signal. Subsequently, the detected magnetic signal of the specimen is transmitted to the control unit, and thereafter a result value is displayed through the display unit.

FIGS. 5(a) to 5(e) are views showing the internal configuration of the detection system of FIG. 4, in which FIGS. 5(a), 5(b), 5(c), 5(d), and 5(e) are a top plan view, a left side view, a front view, a right side view, and a rear view of the detection system, respectively.

Referring to FIG. 5(a), as in the configuration illustrated in FIG. 4, the assay unit 310 receiving the specimen holding unit moves horizontally under the external magnetic-field application device 210. Such a horizontal movement is performed by driving the Y-axis drive motor 330, and is controlled by the control unit 500 that analyzes a signal and controls the drive motor.

FIG. 5(b) is a view when viewing the plan view from the left side. The external magnetic-field application device 210 is formed to be relatively higher than a circuit unit constituting the control unit 500, and the assay unit 310 is provided.

FIG. 5(c) is a view when viewing the plan view from the front, FIG. 5(d) is a right side view, and FIG. 5e is a rear view. Reference numerals common to FIG. 4 and FIGS. 5(a) to 5(e) denote the same components.

Figure 6:
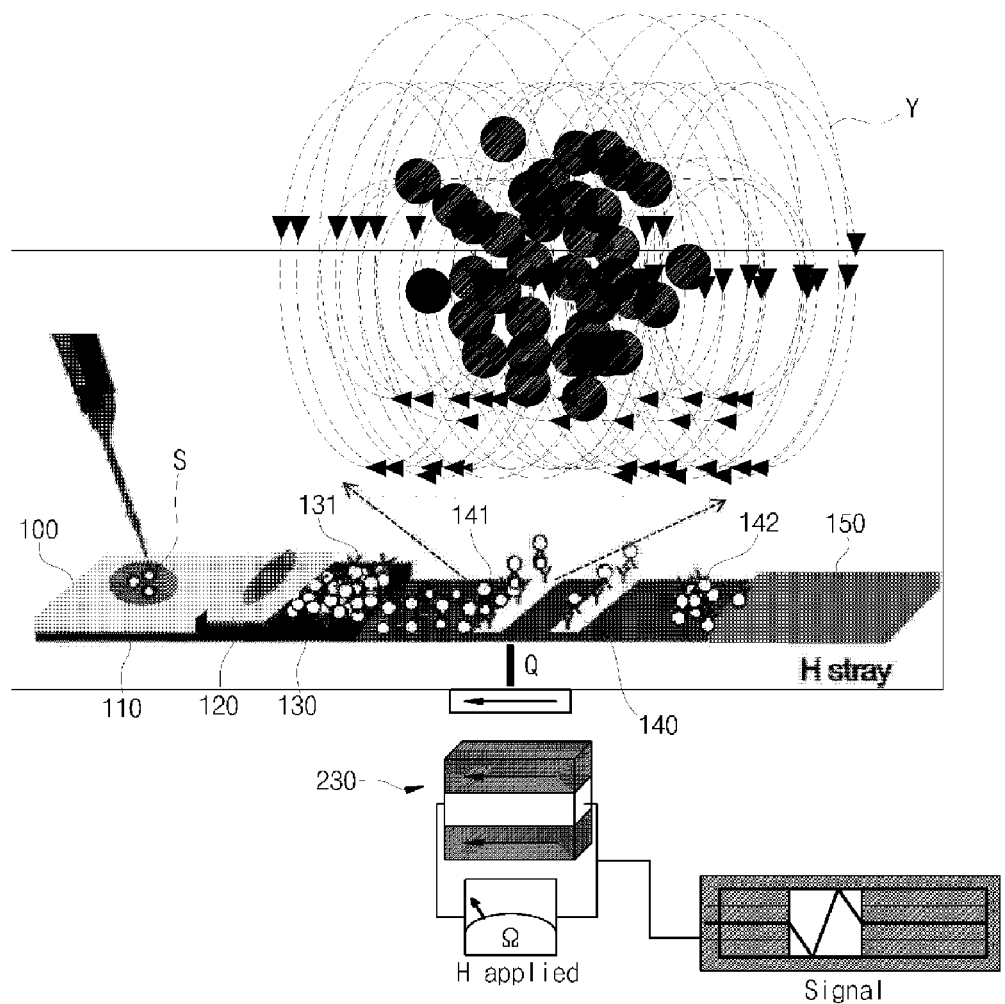
FIG. 6 is a view showing a principle of measurement performed by vertically moving the magnetic resistance sensor using a vertical drive module, after an assay unit of the present invention moves horizontally and stops in a magnetic-field applied space.

FIG. 6 is a view showing a principle of measurement performed by vertically moving the magnetic resistance sensor using the vertical drive module, after the assay unit moves horizontally and stops in a magnetic-field applied space. One example of measurement will be described with a diagnosis kit of immune chromatography performing a blood analysis for POCT. That is, according to this detection example, the specimen holding unit of the above configuration is implemented as the diagnosis kit.

The diagnosis kit 100 corresponding to the specimen holding unit is mounted on the assay unit, and is fed to a detection space under the external magnetic-field application device by the horizontal movement module.

In the diagnosis kit, when a blood sample S is put into an input section 110 and then drops to a separation pad 120, separation of blood corpuscles is performed in the separation pad 120, and primary antigen-antibody binding 131 with nano-magnetic particles occurs in a binding pad 130. After the magnetic particles undergoing the primary binding move to a measurement section 140 of the porous membrane, secondary antigen-antibody binding occurs in the measurement section 140. In this case, the remaining magnetic particles are absorbed by an absorption pad 150.

After the secondary binding is completed, magnetic particles adhering to the membrane pad (measurement section 140) are magnetized by the external magnetic-field application device. A change in magnetic field around the magnetized magnetic particles is measured using the magnetic resistance sensor according to the present invention. At this time, a distance between the diagnosis kit horizontally moving to an area under the external magnetic-field application device and the magnetic resistance sensor 230 must be very accurately adjusted for the purpose of precise measurement. Such a function is performed by the vertical drive module that is driven through the above-mentioned control unit. In the drawing, an image picture Y of the magnetic field shown above the diagnosis kit conceptually illustrates an image of the magnetic field affecting a periphery of the magnetic particles when the secondary binding has been completed in the measurement section.

Preferably, in order to achieve more accurate detection, the assay unit is controlled by the control unit to be reciprocated in the same direction Q as a measuring direction of the magnetic resistance sensor, thus measuring the maximum value of a variable electric signal. The intensity of the measured magnetic field is proportional to protein in blood which is to be measured.

Figure 7:
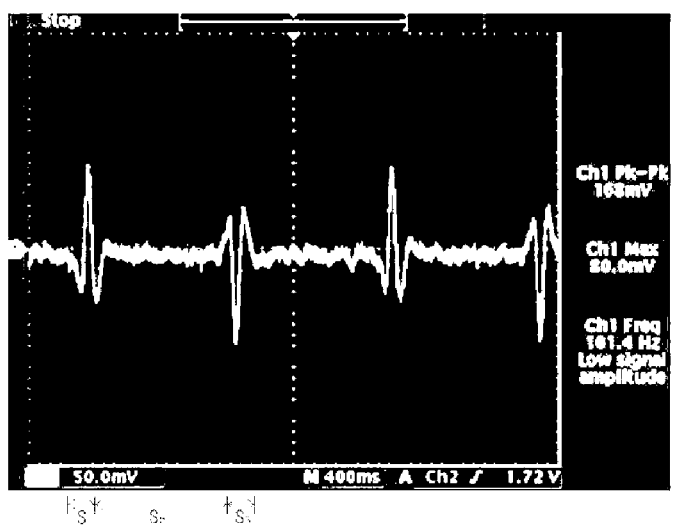
FIG. 7 is a graph illustrating an example of an actual output waveform of the magnetic resistance sensor for a specimen in accordance with the present invention.

FIG. 7 is a graph illustrating an example of an actual output waveform when measuring the maximum value of a variable electric signal by acquiring a difference in signal of the magnetic resistance sensor between the presence and absence of the specimen, while precise distance adjustment between the magnetic resistance sensor and the specimen is performed using the Z-axis drive motor and the specimen holding unit is reciprocated using the Y-axis drive motor. In the drawing, section S 1 represents an output waveform when the magnetic resistance sensor passes through the specimen, section S 2 represents a waveform when the sensor passes through a portion where there is no specimen, and section S 3 represents an output waveform when the sensor passes through the specimen again. As such, the maximum value of the variable electric signal is measured by acquiring a difference in signal of the magnetic resistance sensor between the presence and absence of the specimen.

The external magnetic-field application device is used in the detection system described with reference to FIGS. 2 to 5 to apply external magnetic fields to the magnetic resistance sensor in the first and second directions. The first direction serves to create a horizontal magnetic field, thus setting an initial position of the magnetic resistance sensor, and to block surrounding noise, thus improving performance of the sensor. To be more specific, the external magnetic-field application device preferably includes the first application unit 211 that applies the magnetic field to the magnetic resistance sensor in the first direction, namely, the horizontal direction (Y-axis), and the second application unit 212 that applies the magnetic field to the magnetic resistance sensor in the second direction, namely, the vertical direction (Z-axis). The above-mentioned horizontal and vertical directions are not strictly limited to directions perpendicular to a plane of the magnetic resistance sensor, and are flexible concepts within a permissible range with respect to a given incident direction. Further, the second application unit 212 is preferably embodied to change the magnetic field by a current. A range of the magnetic field applied in the horizontal direction (Y-axis) or a range in which the magnetic resistance (MR) sensor may react may be within 2 to 30 Gauss, and a range of the magnetic field applied in the vertical direction (Z-axis) may be within 1200 to 1800 Gauss.

Thus, the first application unit 211 comprises a magnetic-field generating unit including one or more components selected from a group consisting of a solenoid coil, a Helmholtz coil, an electromagnetic yoke, and a permanent magnet, thus applying a fixed magnetic field. The second application unit 212 comprises a magnetic-field generating unit including one or more components selected from a group consisting of a solenoid coil, a Helmholtz coil, and an electromagnetic yoke, thus applying a magnetic field.

Further, the magnetic resistance sensor 230 of this invention preferably comprises a sensor selected from a group consisting of an ordinary magnetoresistance sensor, an anisotropic magnetoresistance sensor, a giant magnetoresistance sensor, a colossal magnetoresistance sensor, a tunneling magnetoresistance sensor, a magnetic tunneling junction sensor, and a planar hall resistance sensor. It is more preferable to use the giant magnetoresistance (GMR) sensor.

Figure 8:
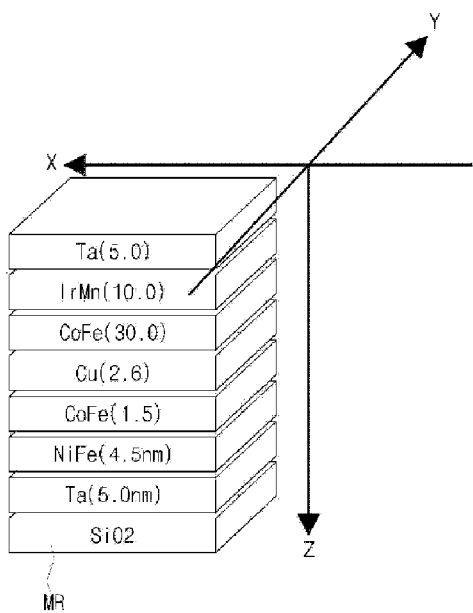
FIGS. 8 and 9 are conceptual views showing a GMR sensor as an embodiment of the magnetic resistance sensor in accordance with the present invention.
Figure 9:
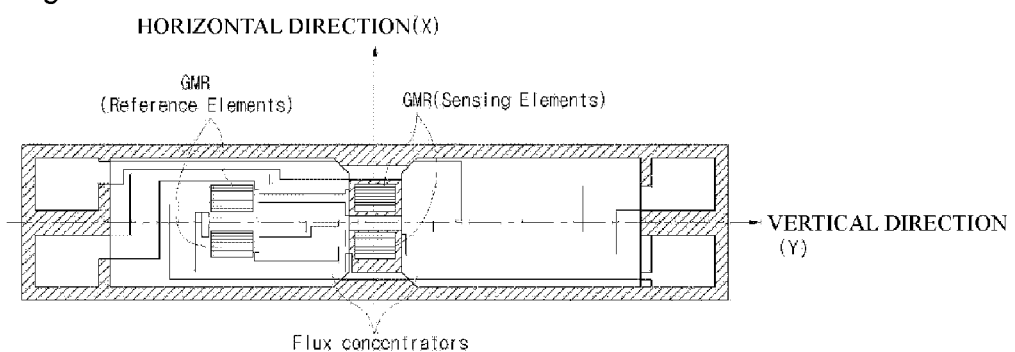

FIGS. 8 and 9 are conceptual views showing a GMR sensor as an embodiment of the magnetic resistance sensor in accordance with the present invention. The drawings illustrate the magnetic resistance sensor used in the detection system. Arrows shown in the drawings designate a horizontal direction (X-axis direction) of foil-type materials, a horizontal direction (Y-axis direction) of foil-type materials, and a vertical direction (Z-axis direction) of foil-type materials, with respect to the sensor formed by layering foil-type materials. Such a GMR sensor is greatly affected only by a magnetic field applied in a direction (Y-axis) perpendicular to the sensor, is slightly affected by a magnetic field applied in a direction (X-axis) parallel to the sensor, and is never affected by a magnetic field applied in a direction (Z-axis) perpendicular to the sensor. Further, it is possible to adjust the biasing of the magnetic field applied in the Y-axis direction within an inherent linear range.

Therefore, in order to realize the maximum performance of the GMR sensor, the system is designed such that a DC magnetic field is applied in the Z-axis direction to saturation magnetize magnetic particles of superparamagnetism, and a magnetic field is applied in the Y-axis direction to adjust biasing and thereby maximize the sensitivity of the sensor. Here, for the application of the magnetic field in the Y-axis direction, it is very effective to use an induced magnetic field generated through DC current. This results in improvement in signal-to-noise ratio.

While the invention has been shown and described with reference to exemplary embodiments thereof, it will be understood by those skilled in the art that various changes in form and details may be made therein without departing from the spirit and scope of the invention as defined by the appended claims. Therefore, the scope of the invention is defined not by the detailed description of the invention but by the appended claims, and all differences within the scope will be construed as being included in the present invention.

The invention claimed is:

1. A detection system using a magnetic resistance sensor, comprising:
    a magnetic resistance sensor for detecting a magnetic element of a specimen containing a magnetic particle;
    an external magnetic-field application device for applying external magnetic fields to the magnetic resistance sensor in first and second directions, the external magnetic-field application device having a space for entrance or exit of a specimen holding unit;
    a horizontal drive module for receiving the specimen holding unit to horizontally move the specimen holding unit under the magnetic resistance sensor; and
    a vertical drive module for receiving the magnetic resistance sensor to vertically move the magnetic resistance sensor to the specimen holding unit.

2. The detection system of claim 1, wherein the horizontal drive module comprises:
    an assay unit for receiving the specimen holding unit; and
    a feeding unit and a Y-axis drive motor for moving the assay unit under the magnetic resistance sensor.

3. The detection system of claim 2, wherein the vertical drive module comprises:
    a support unit for supporting the magnetic resistance sensor; and
    a Z-axis drive motor for vertically moving the magnetic resistance sensor to the specimen holding unit moved by the horizontal drive module.

4. The detection system of claim 3, further comprising:
    a control unit for analyzing a detection signal of the magnetic resistance sensor to control a movement of the drive motor.

5. The detection system of claim 3, further comprising:
    a casing for accommodating the detection system;
    a display unit for displaying an analysis result of the detection signal to an outside of the casing; and
    a printing unit for outputting the analysis result of the detection signal to an outside.

6. The detection system of claim 5, wherein the external magnetic-field application device comprises:
    a first application unit for applying a magnetic field to the magnetic resistance sensor in a horizontal direction (Y-axis) that is the first direction; and a second application unit for applying a magnetic field to the magnetic resistance sensor in a vertical direction (Z-axis) that is the second direction.

7. The detection system of claim 6, wherein the specimen holding unit having the specimen comprises a measuring cartridge or a membrane to which a combination of a magnetic particle and an antibody is fixed.

8. The detection system of claim 6, wherein the first application unit comprises a magnetic-field generating unit including one or more components selected from a group consisting of a solenoid coil, a Helmholtz coil, an electromagnetic yoke, and a permanent magnet, thus applying a fixed magnetic field.

9. The detection system of claim 6, wherein the second application unit comprises a magnetic-field generating unit including one or more components selected from a group consisting of a solenoid coil, a Helmholtz coil, and an electromagnetic yoke, thus applying a magnetic field.

10. The detection system of claim 6, wherein the magnetic field generated by the second application unit is formed by a DC current.

11. The detection system of claim 6, wherein the magnetic resistance sensor comprises a sensor selected from a group consisting of an ordinary magnetoresistance sensor, an anisotropic magnetoresistance sensor, a giant magnetoresistance sensor, a colossal magnetoresistance sensor, a tunneling magnetoresistance sensor, a magnetic tunneling junction sensor, and a planar hall resistance sensor.

12. The detection system of claim 6, wherein the magnetic particle has a magnetization value from 10 to 100 emu/g.

13. The detection system of claim 12, wherein the magnetic particle has superparamagnetism or paramagnetism.

14. The detection system of claim 13, wherein the first application unit has maximum sensitivity at 2 to 30 Gauss.

15. The detection system of claim 13, wherein the magnetic field applied by the second application unit ranges from 1200 to 1800 Gauss.

* * * * *